US009506933B2

(12) United States Patent
Okamoto et al.

(10) Patent No.: US 9,506,933 B2
(45) Date of Patent: Nov. 29, 2016

(54) METHOD OF PREPARING ANTIGEN FOR ACQUIRING ANTI-HYDROPHOBIC PEPTIDE ANTIBODY

(75) Inventors: Masaji Okamoto, Ibaraki (JP); Masato Hanamura, Suwa (JP); Hitoshi Fukushima, Suwa (JP); Tetsuhiko Yoshida, Ibaraki (JP)

(73) Assignees: TOAGOSEI CO., LTD., Tokyo (JP); SEIKO EPSON CORPORATION, Tokyo (JP)

( * ) Notice: Subject to any disclaimer, the term of this patent is extended or adjusted under 35 U.S.C. 154(b) by 484 days.

(21) Appl. No.: 13/978,419

(22) PCT Filed: Jan. 6, 2012

(86) PCT No.: PCT/JP2012/050136
§ 371 (c)(1),
(2), (4) Date: Sep. 19, 2013

(87) PCT Pub. No.: WO2012/093706
PCT Pub. Date: Jul. 12, 2012

(65) Prior Publication Data
US 2014/0072592 A1     Mar. 13, 2014

(30) Foreign Application Priority Data

Jan. 7, 2011   (JP) ................. 2011-002394

(51) Int. Cl.
| C07K 16/18 | (2006.01) |
| G01N 33/68 | (2006.01) |
| C07K 14/245 | (2006.01) |
| C07K 14/47 | (2006.01) |
| C07K 14/705 | (2006.01) |
| C07K 16/12 | (2006.01) |
| C07K 16/28 | (2006.01) |

(52) U.S. Cl.
CPC ......... *G01N 33/6896* (2013.01); *C07K 14/245* (2013.01); *C07K 14/4711* (2013.01); *C07K 14/70596* (2013.01); *C07K 16/1232* (2013.01); *C07K 16/18* (2013.01); *C07K 16/2896* (2013.01)

(58) Field of Classification Search
None
See application file for complete search history.

(56) References Cited

U.S. PATENT DOCUMENTS

| 4,578,269 A | 3/1986 | Morein |
| 4,744,983 A | 5/1988 | Morein |
| 4,981,684 A | 1/1991 | MacKenzie et al. |
| 5,178,860 A | 1/1993 | MacKenzie et al. |
| 5,679,355 A | 10/1997 | Alexander et al. |
| 5,961,970 A * | 10/1999 | Lowell ................. A61K 9/1075 424/184.1 |
| 6,037,521 A | 3/2000 | Sato et al. |
| 2005/0129701 A1 | 6/2005 | Marasco et al. |
| 2010/0074925 A1 | 3/2010 | Carmon |
| 2010/0093059 A1 | 4/2010 | Wolff et al. |
| 2012/0035112 A1 | 2/2012 | Yoshida et al. |
| 2013/0079273 A1 | 3/2013 | Yoshida et al. |
| 2013/0345408 A1 | 12/2013 | Fukushima et al. |
| 2014/0072592 A1 | 3/2014 | Okamoto et al. |
| 2014/0335613 A1 | 11/2014 | Yoshida et al. |
| 2015/0126434 A1 | 5/2015 | Kobayashi et al. |
| 2015/0273018 A1 | 10/2015 | Kobayashi et al. |

FOREIGN PATENT DOCUMENTS

| EP | 0 653 154 | 5/1995 |
| JP | 59-186921 | 10/1984 |
| JP | 07-132033 | 5/1995 |
| JP | 07-505389 | 6/1995 |
| JP | 2005-511047 | 4/2005 |
| JP | 2011-016763 | 1/2011 |
| WO | 03/048337 | 6/2003 |
| WO | 2008/035350 | 3/2008 |
| WO | 2008/125360 | 10/2008 |

OTHER PUBLICATIONS

Hilton et al., "Anti-Peptide Antibody Blocks Peptide Binding to MHC Class I Molecules in the Endoplasmic Reticulum", *Journal of Immunology*, vol. 166, pp. 3952-3956, 2001.
Pomroy et al., "Solubilization of Hydrophobic Peptides by Reversible Cysteine PEGylation", *Biochemical and Biophysical Research Communications*, vol. 245, No. 2, pp. 618-621, 1998.
Boulant et al., "Hepatitis C Virus Core Protein is a Dimeric Alpha-Helical Protein Exhibiting Membrane Protein Features", *Journal of Virology*, vol. 79, No. 17, pp. 11353-11365, 2005.
Extended European Search Report for European Patent Application No. 12731948.1, mailed Jul. 14, 2015.
Kobayashi et al., *J. Biosci. Bioeng.*, vol. 86, pp. 384-386, 2008.
Slivka et al., "Peptide Probes for Protein Transmembrane Domains" *ACS Chem. Biol.* 3(7):402-411, 2008.
http://www.lsbm.org/staff/hamakubo.html, Jul. 30, 2013 (13 pages).
Almen et al., "Mapping the Human Membrane Proteome: A Majority of the Human Membrane Proteins can be Classified According to Function and Evolutionary Origin" *BMC Biology* 7:50, 2009 (14 pages).
http://www.nedo.go.jp/activities/portal/gaiyou/p06009/p06009.html, Dec. 2005 (1 page).
https://ruo.mbl.co.jp/custom/custom#sev.html, copyright 2008, Medical Biological Laboratories (2 pages).
Tam, "Synthetic Peptide Vaccin Design: Synthesis and Properties of a High-Density Multiple Antigenic Peptide System" *Proc. Natl. Acad. Sci. USA* 85:5409-5413, 1988.

(Continued)

*Primary Examiner* — Yunsoo Kim
(74) *Attorney, Agent, or Firm* — Greenblum & Bernstein, P.L.C.

(57) ABSTRACT

The object of the present invention is to provide a method to obtain an antibody for a hydrophobic peptide, which can be used for general purposes easily and with great reliability. Also provided is a method for preparing an antigen characterized in that a hydrophobic peptide, which is unbound to carrier protein, is used as high-molecular-weight aggregates in an aqueous solution containing a nonionic surfactant.

3 Claims, 9 Drawing Sheets

(56) References Cited

OTHER PUBLICATIONS

Beck et al., "Nucleotide Sequence of the Gene ompA Coding the Outer Membrane Protein II* of *Escherichia coli* K-12" *Nucleic Acids Research* 8(13):3011-3027, 1980.

Miraglia et al., "A Novel Five-Transmembrane Hematopoietic Stem Cell Antigen: Isolation, Characterization, and Molecular Cloning" *Blood* 90(12):5013-5021, 1997.

International Search Report for PCT/JP2012/050136, mailed Feb. 28, 2012.

International Preliminary Report on Patentability for PCT/JP2012/050136, mailed Jul. 18, 2013.

* cited by examiner

Column: 4.6mm * 250mm, Hypersil 300A C18
Solvent A: 0.1 % Trifluoroacetic Acid in 100 % Acetonitrile
Solvent B: 0.1 % Trifluoroacetic Acid in 100 % Water
Gradient:          A       B
   0.01 Minutes   32%    68%
   25.0 Minutes   62%    38%
   25.1 Minutes   100%   0%
   30.0 Minutes      STOP
Flow Rate    : 1.0 ml/min
Wave Length : 220nm
Volume       : 5ul

| Rank | Time   | Conc.   | Area    | Ter Tray Number |
|------|--------|---------|---------|-----------------|
| 1    | 13.151 | 0.1358  | 3494    | 98937           |
| 2    | 14.088 | 3.351   | 86246   | 24027           |
| 3    | 14.617 | 1.115   | 28686   | 192785          |
| 4    | 14.760 | 94.38   | 2428723 | 53772           |
| 5    | 15.108 | 0.3534  | 9094    | 229084          |
| 6    | 16.798 | 0.667   | 17166   | 44110           |

Mouse Individual Number

| 41 | 42 | 43 | 44 | 45 |
|----|----|----|----|----|
| 46 | 47 | 48 | 49 | 50 |
| 51 | 52 | 53 | 54 | 55 |
| 56 | 57 | 58 | 59 | 60 |

Dot Blots of Serum (Diluted 500-Fold) Corresponding to Individual Number
(Left Side: 10 ng, Right Side: 100 ng)

A

B

A) Serum of Individual No.6    B) Serum of Individual No.10    C) Serum of Individual No.15

Immunofluorescent Staining of SK-N-SH Cells

A  FCG24/1 % Tween 20 Suspension Measured by Countess

B  1 % Tween 20 Solution Measured by DLS

C  FLF23/1 % Tween 20 Suspension Measured by DLS

SEQUENCE LISTING

```
<160> NUMBER OF SEQ ID NOS: 3

<210> SEQ ID NO 1
<211> LENGTH: 17
<212> TYPE: PRT
<213> ORGANISM: Homo sapiens

<400> SEQUENCE: 1

Met Leu Pro Gly Leu Ala Leu Leu Leu Leu Ala Ala Trp Thr Ala Arg
1               5                   10                  15

Ala

<210> SEQ ID NO 2
<211> LENGTH: 24
<212> TYPE: PRT
<213> ORGANISM: Escherichia coli

<400> SEQUENCE: 2

Phe Gly Gly Tyr Gln Val Asn Pro Tyr Val Gly Phe Glu Met Gly Tyr
1               5                   10                  15

Asp Trp Leu Gly Arg Met Pro Tyr
            20

<210> SEQ ID NO 3
<211> LENGTH: 23
<212> TYPE: PRT
<213> ORGANISM: Homo sapiens
```

```
<400> SEQUENCE: 3

Phe Leu Phe Cys Trp Ile Leu Met Ile Leu Val Val Leu Thr Phe Val
1               5                   10                  15

Val Gly Ala Asn Val Glu Lys
                20
```

METHOD OF PREPARING ANTIGEN FOR ACQUIRING ANTI-HYDROPHOBIC PEPTIDE ANTIBODY

SEQUENCE LISTING

The instant application contains a Sequence Listing which has been submitted in ASCII format via EFS-Web and is hereby incorporated by reference in its entirety. Said ASCII copy, created on Aug. 12, 2013, is named P44027_SL.txt and is 1,180 bytes in size.

TECHNICAL FIELD

The present invention relates to a method of preparing an antigen in the field of immunoengineering.

In particular, the present invention relates to a method of preparing an antigen for acquiring an anti-hydrophobic peptide antibody using a hydrophobic peptide as an immunogen without using a carrier protein.

BACKGROUND ART

Since antibodies have extremely specific molecular recognition ability and high avidity and can easily be produced, with high probability, for a target molecule to be analyzed, antibodies have been utilized as extremely useful research reagents in many laboratories and have been practically utilized in a wide range of applications from diagnostic reagents to pharmaceutical agents for several decades. In many cases, the targets of an antibody are proteins although antibodies have also been utilized for the highly-sensitive detection of target low-molecular-weight compounds such as a certain kind of drug and environmental pollutant.

After the completion of human genome analysis, recently, the expression status and the function of several tens of thousands of gene products are being actively studied in mammalian cells with a focus on human. Several tens of thousands to several hundred thousands of proteins are mixed in tissues and cells. To examine the expression status and localization of a particular one of these proteins, an antibody is essential. In the studies of differentiation and tissue regeneration as well as of cancer cells and stem cells, an antibody has become an indispensable tool as a differentiation marker-detection means for cell sorting in which cells with different functions are fractionated from the same population and for understanding the control of differentiation. Moreover, antibodies are frequently used in basic research of correlation between a particular protein molecule and a certain disease. These studies lead to the development of diagnostic reagents. Antibody drugs are developed from studies on the neutralization of a particular protein molecule and the therapeutic effect on a disease. As described above, antibodies are utilized in a wide range of applications, from basic research to direct practical applications.

To obtain antibodies, animals are usually immunized by antigens. The antigens may be natural or artificial. For natural antigens, a purified target protein or a partially-purified or unpurified mixture containing a target protein is used. On the other hand, major types of artificially prepared antigens are classified into the following two types: (i) a recombinant protein produced by expressing a gene coding the target protein or a fragment thereof in a suitable host and (ii) a synthetic peptide of an amino acid sequence of a portion of the target protein.

The term "peptide" as used herein refers to a peptide with the length of 3 to about 40 amino acids.

If a synthetic peptide is used as an antigen, the time and effort required for antigen preparation can advantageously significantly be reduced due to fewer impurities, as compared to the case of purifying a target protein from natural cells or tissues or the case of utilizing recombinant gene expression. Since the amino acid sequence information is easily available at present with the development of DNA sequencing techniques, immunization using a synthetic peptide as an antigen is frequently utilized. Another advantage of using a synthetic peptide as an antigen is that a particular region of protein can be selected.

The length of a synthetic peptide frequently used as an antigen is usually around 10 to 25 amino acids. To cause an immune reaction, an antigen must bind to the B cell and the class II T cell at the same time (Non Patent Literature 1, P.72). When immunization is performed with a typical immunization schedule, i.e., one administration per one to two weeks, the antigen must remain in the body for more than a certain period of time after administration to an animal. Although the antigen must have at least a certain molecular weight to satisfy these requirements, a peptide generally has a small molecular weight and rapidly metabolized after administration and therefore is not directly used as an antigen.

The immunization with a peptide is disadvantageous in that even if an antibody specifically binding to the peptide is obtained, the antibody does not necessarily have good reactivity to the original protein containing the sequence thereof (Non Patent Literature 1). In this regard, when a peptide is used as an antigen, the probability of acquisition of an intended antibody is lower than when the target protein itself or a fragment thereof (with a molecular weight of about 5000 or more) is used as an antigen and, therefore, two or three different peptide antigen sequences are generally tested.

With regard to which amino acid sequence of the target protein should be selected as a peptide antigen, absolutely certain method is not yet known. As a general selection criteria, one should avoid a position likely to be glycosylated (a region including a motif of Asn-X-Thr or a region rich in Ser or Thr), and select a portion having a relatively high degree of hydrophilicity and likely to come out of a molecular surface or a site containing proline or a bent portion such as the β-turn (Non Patent Literature 1, Non Patent Literature 2).

CITATION LIST

Patent Literature

Non Patent Literature 1: "Antibodies; A LABORATORY MANUAL, Ed Harlow & David Lane, Cold Spring Harbor Laboratory, 1988"

Non Patent Literature 2: Shinobu Ohmi, Kunio Tsujimura, Masaki Inagaki, "Experimental Protocol for Anti-Peptide Antibodies," Shujunsha, 1994

SUMMARY OF INVENTION

Technical Problem

With the recent development of techniques of X-ray structural analysis for protein and techniques of structural analysis for protein molecules in solution by NMR, a multiplicity of protein molecular structures has been revealed. According to these findings, a portion of protein containing a high proportion of hydrophobic amino acid sequences (hydrophobic portion) is hardly dissolved in neutral aqueous solution and keeps a rigid molecular structure. This portion acts as, so to speak, a rigid part to form a core of the steric structure of the protein molecule and plays an important role in generation of integrity and individual characteristics (unique steric structure) of the protein molecule.

The hydrophobic portion of a protein molecule contributes to important intermolecular interactions such as antigen-antibody reactions, ligand-receptor binding, intracellular signal transduction, transport of lipids and low-molecular-weight hydrophobic compounds, and intercellular communication.

A cell is a basic unit of life and separated from the outside by a membrane structure consisting of a lipid bilayer. The cell membrane structure of higher organisms has a large number of complicated membrane structures developed in the course of evolution, not only on the periphery of the cell but also in the cell, such as nucleus, endoplasmic reticulum, Golgi body, and mitochondria and these membrane structures are involved in a variety of important cellular functions. The membrane structure constructs the shape of the cell and expresses unique special functions to be involved in higher-order life activities such as differentiation and morphogenesis.

It is estimated that 27% of all the protein species of the cell are membrane proteins and, as can be seen from the localization in a state of being embedded in the lipid bilayer, the membrane protein is rich in hydrophobic sequences. With regard to the overall structure of the membrane protein, 1- to 12-transmembrane types are known (Non Patent Literature 3). When the number of times of membrane penetration is larger, the rate of hydrophobic amino acids in the protein is higher. These transmembrane proteins are related to receptors of ligands transferring an extracellular signal to the cell, receptors of neurotransmitters and drugs, and transporters. Moreover, these transmembrane proteins are involved in tissue formation such as intercellular recognition, differentiation, and morphogenesis.

At least 60% or more of medical drugs currently target membrane proteins (Non Patent Literature 4) and it is known that multi-transmembrane membrane proteins function in the lipid bilayer and therefore include a higher proportion of the hydrophobic portion.

As described above, the need for the research for acquiring useful information on membrane proteins is high, which inevitably increases the need for efficiently producing practical anti-membrane protein antibodies. For example, NEDO (New Energy and Industrial Technology Development Organization) is conducting the research called "Development of New Functional Antibody Technologies" (project period: FY 2006 to FY 2010; FY 2009 budget: 900 million yen; PL: Tatsuhiko Kodama (Professor, Research Center for Advanced Science and Technology, University of Tokyo), Non Patent Literature 5).

Non Patent Literature 3: M. S. Almen et al, *BMC biology* 7:50, doi: 10.1186/1741-7007-7-50, This article is available from: www.biomedcentral.com/1741-7007/7/50

Non Patent Literature 4: P. F. Slivka et al., *ACS Chem. Biol.*, 2008, 3 (7), pp. 402-411

Non Patent Literature 5: www.nedo.go.jp/activities/portal/gaiyou/p06009/p06009.html Other known methods will be described below.

Other than the membrane proteins, proteins functioning outside the cell, inside the nucleus, and in other subcellular organelles move through the cellular membrane. At least a signal peptide and a localization peptide sequence are involved in the control of intracellular movement and metabolism of these proteins (O. Bakke and T. W. Nordeng, Immunol Rev. 172:171-87, 1999). The signal peptide generally contains a highly hydrophobic portion therein.

As described above, a highly hydrophobic amino acid sequence is considered as being buried in the molecule and therefore is conventionally avoided when a candidate sequence is selected for the production of an anti-peptide antibody. Even if a peptide consisting of a hydrophobic amino acid sequence is synthesized, the peptide is hardly handled in a state of neutral aqueous solution due to poor water solubility and it is often difficult to use the peptide in a crosslinking reaction with carrier protein and, because of these problems, the hydrophobic amino acid sequence is further avoided when an antigen is selected. Thus, it is extremely difficult to select, as a candidate of an immunogen, a sequence portion containing a high proportion of highly hydrophobic amino acid sequences in the signal peptide and in the membrane protein, and therefore, an antibody to such a sequence has almost never been produced despite its importance.

Another reason making the acquisition of the antibody to membrane protein difficult is that since an extracellular hydrophilic portion of membrane protein of higher organisms is often glycosylated, even if an anti-peptide antibody recognizing a synthetic peptide can be produced by immunization with the synthetic peptide, the native antigen protein is often not recognized.

A means in the case of performing immunization without using a synthetic peptide can be implemented by totally synthesizing or cloning cDNA of the protein, expressing the protein in a suitable host by using the cDNA for a recombinant gene, and purifying and using the acquired protein in the immunization. However, it is problematic that this method often leads to a lower expression level of the membrane protein and that the membrane protein itself makes the purification relatively difficult.

Another immunization method is a method called DNA immunization (Non Patent Literature 6). In this method, cDNA coding an intended protein is cloned in a plasmid vector having a cloning site located downstream of a promoter that can be expressed in mice for immunization with plasmid DNA; however, it is problematic that the probability of success of immunization is not high and that the method is unusable for intracellularly-localized membrane protein and is time-consuming.

Although a method exists that expresses an intended protein in the baculovirus envelope for immunization with virus particles, this method is also time-consuming (Non Patent Literature 7).

Although a method exists that expresses an intended protein in a suitable cell by using a recombinant virus so as to use a whole cell in the immunization, this method requires a special technique and a considerable effort (Non Patent Literature 8).

A peptide itself is not suitable for an antigen because its molecular weight is too small and, therefore, the molecular weight must be increased. Thus, a peptide and a carrier protein are normally cross-linked and used as an antigen. MBS (m-Maleimidobenzoyl-N-hydroxysuccinimide ester) crosslinking between amino and sulfhydryl groups and EDC (1-ethyl-3-(3-dimethylaminopropyl carbodiimide hydrochloride) crosslinking between amino and carboxyl groups are known as commonly used crosslinking agents (Non Patent Literature 1). Glutaraldehyde bisimide ester is also used in some cases. These reactions are usable in aqueous solution at around pH 5 for EDC and pH 7 to 8 for the other reagents (Non Patent Literature 1). Since poorly-soluble or insoluble hydrophobic peptides cannot contribute to a reaction under such conditions, conjugates cannot successfully be produced.

A method without using a carrier protein for an antigen is reported as an MAP (Multiple Antigen Peptide) method in which the amino group of lysine is utilized for branching during the peptide synthesis so as to synthesize an octamer (Non Patent Literature 9). This method is disadvantageous in that the synthesized MAP peptide does not form a single peak in HPLC and cannot be purified, that the peptide becomes insoluble if the number of amino acids is equal to or greater than ten, and that the titer is often not increased (Non Patent Literature 10).

As described above, a simple and reliable method which can be used in a versatile manner has not yet been developed for the purpose of acquiring an antibody to a hydrophobic peptide.

Non Patent Literature 6: Takeshi Kobayashi, J. Biosci. Bioeng., volume 86, pp. 384-386 (2008)
Non Patent Literature 7: www.lsbm.org/staff/hamakubo.html
Non Patent Literature 8: ruo.mbl.co.jp/custom/custom#sev.html
Non Patent Literature 9: Tam, J. P.: Synthesis and properties of a high-density multiple antigenic peptide system, Proc. Natl. Acad. Sci. USA, 85, 5409-5413 (1988)
Non Patent Literature 10: Shinobu Ohmi, Kunio Tsujimura, Masaki Inagaki, "Experimental Protocol for Anti-Peptide Antibodies," Shujunsha, 1994

Solution to Problem

As a result of extensive research for solving the problems, the inventors focused attention on suspending hydrophobic peptides in a neutral aqueous solution containing a nonionic surfactant. The inventors discovered that, in such a solution, a peptide containing a highly hydrophobic sequence was not dissolved into individual molecules and was present as high-molecular-weight aggregates even when the solution was visually transparent. A large portion of the high-molecular-weight aggregates has a molecular weight equal to or greater than 10 kDa and some of the aggregates have a particle size (diameter) of several nm to several tens of μm. When such a high-molecular-weight aggregate solution was used for direct immunization of animals other than human without creating a conjugate with a carrier protein, the inventors surprisingly discovered that an antibody specifically recognizing the peptide sequence of the antigen could be obtained, thereby completing the present invention.

The present invention has the following configurations.

(1) A method of preparing an antigen, wherein a hydrophobic peptide unbound to carrier protein is turned into high-molecular-weight aggregates in an aqueous solution containing a nonionic surfactant.

(2) The method of preparing an antigen of (1) above, wherein the nonionic surfactant is at least one selected from the group consisting of polyoxyethylene (20) sorbitan monolaurate, polyoxyethylene (20) sorbitan monooleate, polyoxyethylene (8) octylphenyl ether, polyoxyethylene (9) octylphenyl ether, polyethylene glycol (12), polyethylene glycol (24), polyethylene glycol (60) dodecyl ether, and polyethylene glycol cholesterol derivatives.

(3) The method of preparing an antigen of (1) or (2) above, wherein 20% by mass or more of the high-molecular-weight aggregates of hydrophobic peptide in the aqueous solution containing the nonionic surfactant has a molecular weight equal to or greater than 100 kDa.

(4) The method of preparing an antigen of any one of (1) to (3) above, wherein the hydrophobic peptide is a peptide which forms aggregates having molecular weights equal to or greater than 10,000 rather than takes a monomeric form when added to pure water.

(5) The method of preparing an antigen of any one of (1) to (4) above, wherein the sequence of the hydrophobic peptide is MLPGLALLLLAAWTARA (SEQ ID NO: 1), FGGYQVNPYVGFEMGYDWLGRMPY (SEQ ID NO: 2), or FLFCWILMILVVLTFVVGANVEK (SEQ ID NO: 3).

(6) The method of preparing an antigen of any one of (1) to (5) above, comprising the following steps 1) and 2):
1) suspending the hydrophobic peptide unbound to carrier protein in pure water; and
2) adding the nonionic surfactant to suspension obtained at 1).

(7) An antibody obtainable by immunizing a nonhuman mammal with an antigen prepared by the method of any one of (1) to (6) above.

(8) The antibody of (7) above, wherein the antibody is a monoclonal antibody.

(9) A method of detecting an antigen present in a sample, comprising the step of bringing the antibody of (7) above into contact with the sample.

(10) The method of (9) above, wherein the antigen is an amyloid precursor protein signal peptide (SPAPP, hereinafter sometimes simply referred to as SPAPP), and wherein the antibody is an anti-amyloid precursor protein signal peptide monoclonal antibody (anti-SPAPP monoclonal antibody).

(11) A method of manufacturing an antibody comprising the step of administering an antigen prepared by the method of any one of (1) to (6) to a nonhuman mammal.

Advantageous Effects of Invention

According to the method of the present invention, by using a hydrophobic peptide which is expected to have poor antigenicity and has been avoided for years because handling in aqueous solution is difficult, an antibody to the hydrophobic peptide is obtained. According to the method of the present invention, since the cost and time for binding a carrier protein and a hydrophobic peptide to create a conjugate is not needed, economic efficiency is increased. If immunization is performed by using a carrier protein, an antibody to the carrier protein is inevitably generated; however, a carrier protein is not used in the method of the present invention and, therefore, the intended antibody can be obtained with high efficiency.

Since the present invention enables the acquisition of an antibody to a hydrophobic peptide, new useful information on hydrophobic signal peptides and membrane proteins, in terms of physiological roles such as metabolic pathways, subcellular localization and interaction partners, which has previously not been available can be obtained. The useful information obtained in this way is highly likely to contribute to the understanding of cellular functions and the development of diagnostic reagents and pharmaceutical agents. Although the acquisition of an antibody to a membrane protein is extremely difficult in a conventional manner, the present invention will effectively and significantly reduce the effort and cost.

DESCRIPTION OF EMBODIMENTS (Hydrophobic Peptide)

Figure 1:
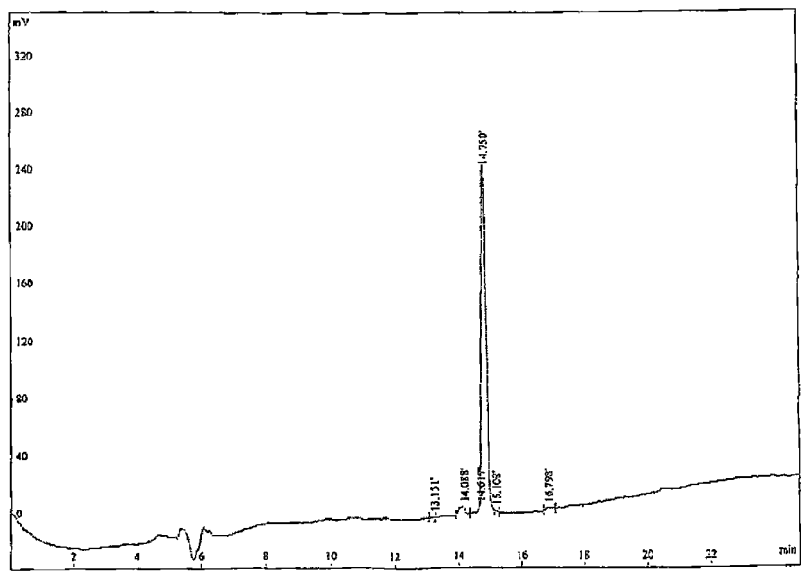
FIG. 1 depicts an HPLC chromatogram of purified SPAPP.

A peptide used as an antigen in the method of preparing an antigen of the present invention can be any peptide as long as the peptide is a hydrophobic peptide and is characterized in that the peptide is a hydrophobic peptide unbound to carrier protein. In other words, the method of preparing an antigen of the present invention is a method using only a hydrophobic peptide as an antigen without using a carrier protein.

Hydrophilicity/hydrophobicity profile of a peptide to be used as an antigen in the present invention is basically found out by examining the amino acid sequence of the target protein. Amino acid sequences can be examined on web sites (such as Protscale of ExPASy Proteomics tools (HYPERLINK expasy.org/tools/protscale.html)) and commercially available gene analysis software (such as the gene information processing software "GENETYX" of GENETYX Corporation). The hydrophobic peptide used in the present invention is a peptide determined as being hydrophobic based on the hydrophobicity/hydrophilicity analysis results and, strictly speaking, is a peptide which forms aggregates having molecular weights of 10,000 or more, rather than takes a monomeric form, when mixed with pure water. The presence of aggregates and approximate molecular weight distribution can be confirmed by processing a peptide solution with a centrifugal ultrafiltration unit with a molecular weight cutoff of 10,000 such as Amicon Ultra-0.5 and PLGC Ultracel-10 membranes and comparing peptide concentrations between an original solution and a permeation solution. The presence of aggregates and approximate molecular weight distribution can also be analyzed with HPLC by using a gel filtration column with a proper fraction range.

A hydrophobic peptide used as an antigen of the present invention can be synthesized by an F-MOC-method peptide synthesizer, and then, separated, purified, and fractionated with acetonitrile concentration gradient by C18 HPLC column. These procedures can be delegated to a contract manufacturer of synthetic peptides. In this description, an antibody to a peptide is referred to as an "anti-peptide antibody" and, particularly, as an "anti-hydrophobic peptide antibody" when it is limited to an antibody to a hydrophobic peptide.

(Aggregate of Hydrophobic Peptides)

Any hydrophobic peptides can be used as an antigen in the present invention as long as the hydrophobic peptide forms high-molecular-weight aggregates in a neutral aqueous solution containing a nonionic surfactant. Although the degree of aggregation and the particle size of aggregates may vary depending on the hydrophobic sequence of the peptide used as an antigen, a large portion of peptide aggregates more preferably has a molecular weight of 10,000 to 20,000 or more. A larger molecular weight within a handleable range is more desirable. In this description, an aggregate formed from peptides noncovalently bound to each other may as a whole be referred to as a "molecule" and a solution containing peptides in a state of aggregates may be referred to as a "solution" or "suspension". As in the Examples described later, according to the method of preparing an antigen of the present invention, a hydrophobic peptide alone is recognized as an antigen and an antibody to the peptide (also referred to as an anti-peptide antibody) can be obtained without creating a conjugate between the hydrophobic peptides and carrier protein. In other words, if several or more peptides form an aggregate in aqueous solution to form a molecule with a molecular weight equal to or greater than about 10,000, the peptide is recognized as an antigen in an immune reaction, and the antibody to the antigen can be obtained. As described above, according to the method of the present invention, an antibody to a hydrophobic peptide (also referred to as an anti-hydrophobic peptide antibody) can be obtained regardless of the type of a nonionic surfactant, without limiting the concentration thereof to a particular concentration, and without limiting the target to a specific amino acid sequence.

(Method of Preparing Antigen)

The method of preparing an antigen of the present invention is performed by the following steps, for example.

1) A hydrophobic peptide is added to pure water and mixed well by a mixer and, if opaque, ultrasound is applied for making it partially transparent.

2) A nonionic surfactant is added to the pure water suspension of the hydrophobic peptide obtained at 1) to produce high-molecular-weight aggregates of the hydrophobic peptide.

High-molecular-weight aggregates having molecular weights equal to or greater than 10,000 (10 kDa) must account for a large portion in the molecular weight distribution. Preferably, it is desirable to prepare the suspension such that those having molecular weights equal to or greater than 100,000 (100 kDa) account for 20% by mass or more of the total peptide mass. The molecular weight distribution can roughly be grasped by combining gel filtration or the use of centrifugal molecular weight cutoff membrane with the BCA or a protein (peptide) concentration assay (as in Examples), or by Native PAGE.

The high-molecular-weight aggregates desirably include particles of 1 μm to 100 μm in the particle size distribution. The particle size distribution can be examined by a device utilizing dynamic light scattering such as a dynamic light scattering particle size analyser or a cell counter such as Countess™ (Invitrogen) Coulter counter.

The time until the addition of the surfactant after suspending the hydrophobic peptide in pure water affects the subsequent aggregate molecular weight distribution. Thus, if the surfactant is added without an interval, the molecular weight distribution of the aggregates tends to be lower and if a sufficient interval is taken in a pure water suspension state, the aggregates tend to be distributed on the higher molecular weight side. The size distribution of the hydrophobic peptide aggregates can be controlled in such a manner.

(Nonionic Surfactant)

The surfactant for producing the high-molecular-weight aggregates of hydrophobic peptide of the present invention may be any nonionic surfactant and includes, for example, polyoxyethylene (20) sorbitan monolaurate (Tween 20), polyoxyethylene (20) sorbitan monooleate (Tween 80), polyethylene glycol (12) (PEG12), polyethylene glycol (24) (PEG24), polyethylene glycol (60) (PEG60) dodecyl ether, polyethylene glycol cholesterol derivatives represented by the general formula shown below, polyoxyethylene (8) octylphenyl ether (Triton X-100), polyoxyethylene (9) octylphenyl ether (Nonidet P-40), β-octylglucoside, dodecyl-β-D-maltoside, and the commercially available nonionic surfactants described below. Among these surfactants, polyoxyethylene (20) sorbitan monolaurate, polyoxyethylene (20) sorbitan monooleate, polyoxyethylene (8) octylphenyl ether, polyoxyethylene (9) octylphenyl ether, polyethylene glycol (12), polyethylene glycol (24), polyethylene glycol (60) dodecyl ether, or polyethylene glycol cholesterol is preferably used. The nonionic surfactant used in the present invention may be added to the solution of hydrophobic peptide suspended in pure water, or a nonionic surfactant aqueous solution may be prepared before adding the hydrophobic peptide to prepare the high-molecular-weight aggregates of hydrophobic-peptide. The molecular weight distribution of high-molecular-weight aggregates of hydrophobic-peptide also varies depending on the sequence of hydrophobic peptide, the type of nonionic surfactant, or the concentration of nonionic surfactant. The concentration of nonionic surfactant may be within any range allowing a wide distribution of particle size of the high-molecular-weight aggregates of hydrophobic-peptide and preferably ranges roughly from 0 to 2% by mass, for example.

[Chem 1]

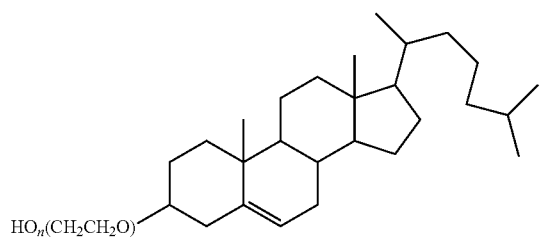

(Examples of Commercially Available Nonionic Surfactant)

N,N-Bis(3-D-gluconamidopropyl) cholamide [BIGCHAP], Dojindo Laboratories;

342-05611 N,N-Bis(3-D-gluconamidopropyl) deoxycholamide [Deoxy-BIGCHAP], Dojindo Laboratories;

149-05701 NIKKOL BL-9EX [Polyoxyethylene (9) Lauryl Ether], Wako special grade;

348-05071 Octanoyl-N-methylglucamide [MEGA-8], Dojindo Laboratories;

345-05081 Nonanoyl-N-methylglucamide [MEGA-9], Dojindo Laboratories;

342-05091 Decanoyl-N-methylglucamide [MEGA-10], Dojindo Laboratories;

348-05093, Dojindo Laboratories;

164-19881 Polyoxyethylene (8) Octylphenyl Ether [Triton X-114], for biochemistry;

161-19911 Polyoxyethylene (9) Octylphenyl Ether [NP-40], for biochemistry;

168-11805 Polyoxyethylene (10) Octylphenyl Ether [Triton X-100];

163-11512 Polyoxyethylene (20) Sorbitan Monolaurate [Tween 20];

160-11522 Polyoxyethylene (20) Sorbitan Monopalmitate [Tween 40];

167-11532 Polyoxyethylene (20) Sorbitan Monostearate [Tween 60];

164-11542 Polyoxyethylene (20) Sorbitan Monooleate [Tween 80];

161-11552 Polyoxyethylene (20) Sorbitan Trioleate Pr.G.;

160-11561 Polyoxyethylene (23) Lauryl Ether [Brij35];

533-80981 CALBIOCHEM;

167-11571 Polyoxyethylene (20) Cethyl Ether [Brij58];

341-06161 n-Dodecyl-β-D-maltopyranoside, Dojindo Laboratories;

346-05371 n-Heptyl-β-D-thioglucopyranoside, Dojindo Laboratories;

340-05031 n-Octyl-β-D-glucopyranoside, Dojindo Laboratories;

349-05361 n-Octyl-β-D-thioglucopyranoside, Dojindo Laboratories;

343-06861 n-Nonyl-β-D-thiomaltoside, Dojindo Laboratories;

043-21376 Digitonin, for biochemistry; and 192-08851 Saponin, from Soybeans, Wako first class grade.

(Immunization)

Immunization may be performed in accordance with a technique typically conducted by those skilled in the art. Blood collection may be performed to measure serum titer, and the period of immunity may be extended. A serum titer can be examined by dot blot of antigen peptide or by EIA using an antigen peptide conjugate-coated plate or an antigen peptide-coated plate. A serum titer can also be assayed by Western blotting or immunostaining depending on the purpose. Although the immunogen of the present invention is prepared by a method of obtaining aggregates by adding a hydrophobic peptide to a nonionic surfactant without using a carrier protein, it is obvious that this does not exclude the use of a conjugate between a carrier protein and the peptide in preparation of an antigen peptide conjugate-coated plate or an antigen peptide-coated plate for measuring the titer of an antibody.

(Monoclonal Antibody)

Description will be made of a method of obtaining a monoclonal antibody to a hydrophobic peptide from a mammal immunized by using as an antigen the highmolecular-weight aggregates of the hydrophobic peptide obtained by the method of preparing an antigen described above.

Although experimental animals such as guinea pigs, rats, mice, rabbits, and sheep are used as the mammals to be immunized, rats, mice, and rabbits are preferred for obtaining monoclonal antibodies or polyclonal antibodies. Although any administration route, for example, subcutaneous, intraperitoneal, intravenous, intramuscular, or intradermal route may be used in the immunization method, the antigen is preferably mainly injected subcutaneously, intraperitoneally, or intravenously. The immunization interval, the immunization dose, etc., are not particularly limited and various methods may be used. In many cases, however, for example, immunization is performed a total of about 2 to 10 times at intervals of 2 weeks and, after the last immunization (preferably, after about 2 to 7 days), samples are collected from the living body for about 1 to 5 times. Although the peptide amount per administration is not limited, the immunization dose is preferably about 10 to 200 µg of peptides per mouse. At initial immunization, the high-molecular-weight aggregates of a hydrophobic peptide are mixed well with adjuvant (e.g., Freund's complete adjuvant) and intraperitoneally administered to mice to grow cells; the high-molecular-weight aggregates are mixed well again with adjuvant (e.g., Freund's incomplete adjuvant) and intraperitoneally administered at intervals of two weeks; and blood, ascites, and antibody production cells can subsequently be collected to efficiently obtain anti-hydrophobic peptide monoclonal or polyclonal antibodies of high titer. The intended monoclonal antibodies or polyclonal antibodies can be purified by a known method such as affinity chromatography, ion exchange chromatography, gel filtration, and ammonium sulfate precipitation.

Description will be made of a method of detecting a hydrophobic peptide of interest from samples based on an antigen-antibody reaction using an antibody obtained by the method of manufacturing an antibody to a hydrophobic peptide. The sample may be in any form and can be a biological sample prepared from blood supernatant, serum, plasma, lymph fluid, urine, cerebrospinal fluid, saliva, sweat, ascites, amniotic, or extraction liquid from cells or organs, for example. The biological sample can appropriately be processed as needed. For example, to a sample acquired by separation of cells or extraction operation, a known method such as immunohistochemical staining, enzyme immunoassay, a coagulation method, a competition method, and a sandwich method are applicable. The immunohistochemical staining may be performed with a direct method using a labeled antibody and an indirect method using an antibody obtained by labeling an antibody to the antibody, for example. Any known labeling substances such as fluorescent material, radioactive substances, enzymes, metals, and dyes can be used as a labeling agent.

(Conjugate)

The term "conjugate" as used herein means a complex obtained by chemical cross-linking between a carrier protein and an antigenic peptide. Typically, when a peptide is used as an antigen, to increase turnover time, the antigen is chemically cross-linked to a carrier protein having an effect of causing binding to class II T cells and is used as a conjugate (Non Patent Literature 1). KLH (keyhole-limpet hemocyanin), BSA (bovine serum albumin), ovalbumin, etc., are used as the carrier protein (Non Patent Literature 1).

For cross-linking, MBS (m-Maleimidobenzoyl-N-hydroxysuccinimide ester), NHS(N-hydroxysuccinimide ester), EDC (1-ethyl-3-(3-dimethylaminopropyl) carbodiimide), glutaraldehyde, etc., are used. The cross-linking is achieved by causing covalently bonding —SH of the cysteine residue and the amino group in the case of MBS, the amino group and the amino group in the case of NHS, the amino group and the carboxyl group in the case of ECD, or the amino groups to each other in the case of glutaraldehyde (forming imine binding between). To contribute to these cross-links, free functional groups are required.

EXAMPLES

Test Example 1

Synthesis, Purification, and Accurate Mass Confirmation of Hydrophobic Peptide SPAPP (Amyloid Precursor Protein Signal Peptide)

Figure 2:
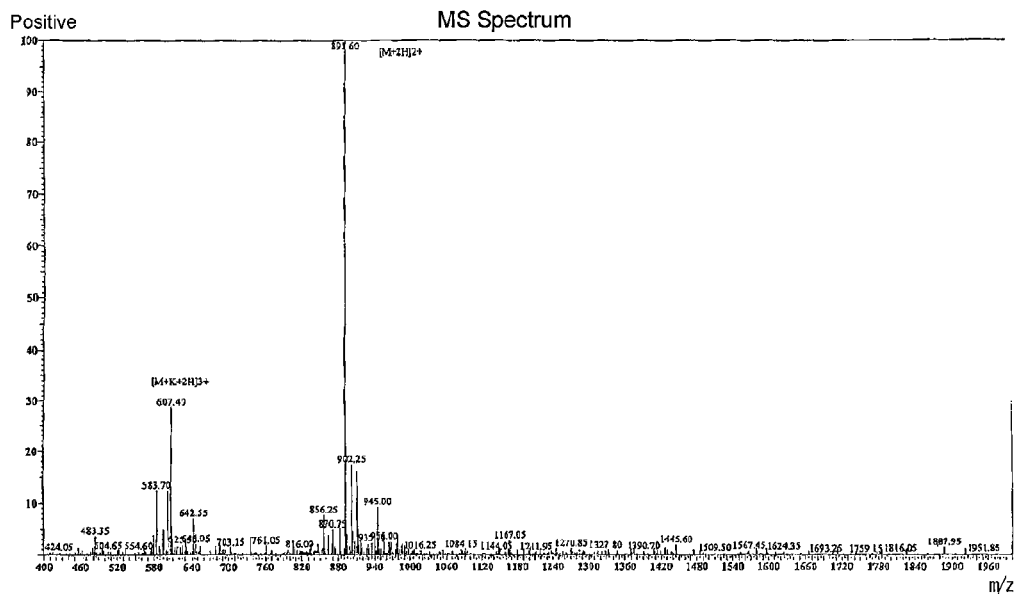
FIG. 2 depicts an LC-MS chromatogram of purified SPAPP.

The peptide MLPGLALLLLAAWTARA-COOH consisting of a sequence (SEQ ID NO: 1) of first (1) to seventeenth (17) positions, which is considered to be the signal peptide of the human amyloid precursor protein A4, was synthesized and purified by consignment to GL Biochem (Shanghai) Ltd. The purity of the purified polypeptide was 92% to 94% from the HPLC peak area ratio (FIG. 1). With regard to the molecular weight, a divalent ion signal of 891.5 or a monovalent ion signal of 1781 was observed from LC-MS (ESI mode) (FIG. 2), which indicates a mass of 1781. This was consistent with the molecular weight calculated from the amino acid sequence and it was confirmed that the peptide was the intended peptide.

Test Example 2

Test of Solubility of Peptide SPAPP to Various Solvents (1) Powdered purified SPAPP was mixed with various solvents at various concentrations to examine solubility. Table 1 shows the test conditions and results.

The term "soluble" used in the following description means a state in which solvent is visually transparent and "insoluble" means a state in which solvent is visually cloudy.

TABLE 1

| Solvent classification | Solvent name | SPAPP conc. | Solubility |
| --- | --- | --- | --- |
| Neutral aqueous solution | Pure water | 0.1 mg/ml | Insoluble |
|  | Phosphate buffer (PBS) (pH 7) |  | Insoluble |
| Strongly acidic aqueous solution | 0.1% trifluoroacetic acid (pH 2.0) | 7.5 mg/ml | Soluble |
|  | 1% formic acid (pH 3.0) | 0.5 mg/ml | Soluble |
| Organic solvent | 100% methanol | 0.5 mg/ml | Soluble |
|  | 100% DMSO | 50 mg/ml | Soluble |
|  | 100% DMF | 20 mg/ml | Soluble |
| Surfactant (anionic) | 1% SDS | 1~5 mg/ml | Soluble |
| (nonionic) | 1% Tween20 | 1~5 mg/ml | Soluble |
| (nonionic) | 1% Tween80 | 1~5 mg/ml | Soluble |
| (nonionic) | 1% TritonX-100 | 1~5 mg/ml | Soluble |
| (nonionic) | 1% Nonidet P40 | 1~5 mg/ml | Soluble |
| (nonionic) | 1% PEG12 | 1~5 mg/ml | Soluble |
| (nonionic) | 1% PEG24 | 1~5 mg/ml | Soluble |
| (nonionic) | 1% PEG60 docesylether | 1~5 mg/ml | Soluble |

TABLE 1-continued

| Solvent classification | Solvent name | SPAPP conc. | Solubility |
|---|---|---|---|
| (nonionic) | 1% cholesterol-PEG (NOF CORPORATION NO. CS050) | 1~5 mg/ml | Soluble |

(2) Results and Discussion (i) Neutral Aqueous Solutions

SPAPP became cloudy and was completely insoluble in neutral aqueous solutions.

(ii) Strongly Acidic Aqueous Solutions

The isoelectric point of SPAPP is 10.9 and was soluble in strongly acidic aqueous solutions.

(iii) Organic Solvents

SPAPP was soluble in polar organic solvents.

(iv) Neutral Aqueous Solutions Containing Surfactant

SPAPP was soluble in neutral aqueous solutions containing polar and nonionic surfactants.

(v) From these results, it is considered that, while SPAPP is insoluble in neutral aqueous solutions and forms large aggregates causing cloudy solutions due to high hydrophobicity, SPAPP becomes soluble even in neutral aqueous solution through the mediation of molecules hydrating SPAPP (i.e., surfactant). In such state, as described later, even if aqueous solution is visually transparent, SPAPP is present as high-molecular-weight aggregates in the aqueous solution.

Although the hydrophobic peptide was soluble in aqueous solution containing a polar surfactant, no antibody was obtained from immunization using this solution (data not shown) and, therefore, it is considered that a nonionic surfactant is preferable as the surfactant. The strongly acidic aqueous solutions and the organic solvents are reference examples.

Test Example 3

Antibody Titer Measurement Test Method Using Dot Blotting (1) Dot blotting was performed with the following procedure.

(i) A nitrocellulose membrane was spotted with 1 Tween 20 solution of SPAPP at 1 µl/dot and the nitrocellulose membrane was blocked by 1% skim milk/TBST or Starting Block (TBS) Blocking Buffer at room temperature for one hour or more.

(ii) Serum to be examined in terms of titer was diluted by a factor of 400 to 500 with 0.2% skim milk/TBST, added to the nitrocellulose membrane spotted with SPAPP, and shaken at room temperature (20 to 24° C.) for one hour for a primary antibody reaction.

(iii) Unbound unreacted antibodies were removed by washing the nitrocellulose membrane 3 times for 5 minutes each with 0.2% skim milk/PBST.

(iv) A secondary antibody reaction was caused by shaking the nitrocellulose membrane for one hour along with secondary antibodies diluted by a factor of 4,000 with 0.2% skim milk/TBST.

(v) The nitrocellulose membrane was washed 3 times for 5 minutes each with 0.2% skim milk/TBST.

(vi) Alkaline phosphatase substrate solution was added to cause a color reaction at room temperature for 30 minutes and the reaction was stopped by washing with pure water.

(2) Materials and Reagents

Secondary Antibody

In the case of mouse serum: Anti-Mouse IgG (Fc specific) Alkaline Phosphatase Conjugate (Sigma No. A-2429)

In the case of rabbit serum: Goat Polyclonal Anti-Rabbit Immunoglobulins AP (DAKO No. D0487)

Alkaline phosphatase substrate solution: Thermo Scientific, No. 34042 1-Step NBT/BCIP TBS: 10 mM Tris-HCl pH 7.5, 0.1 M NaCl TBST: TBS+1% Tween 20

Nitrocellulose membrane: Hybond-ECL manufactured by GE Healthcare

Starting Block (TBS) Blocking Buffer: No. 37542 manufactured by Thermo Scientific Comparative Example Measurement of Titers of Serum (Polyclonal Antibodies) Obtained by Using Various Conjugates as Immunogen (Conventional Method)

Conjugates were produced between SPAPP and various carrier proteins to measure titers by using serum obtained by using these conjugates in immunization.

(1) SPAPP/KLH Conjugate (1-1) Production of Conjugate

By dissolving 2.5 mg KLH (Wako Pure Chemical Industries, Ltd., No. 08607663) into 66 µl of 1.5 M NaCl and mixing 70 µl of 1 M MES buffer (pH 4.5) and 565.5 µl of pure water, KLH solution was prepared at a final concentration of 3.77 mg/ml. SPAPP solution was prepared by dissolving SPAPP into 100% DMSO to a concentration of 7.5 mg/ml. EDC solution was prepared with pure water at 33 mg/ml. These solutions were mixed in the following volumes and order and allowed to stand for 15 hours at 23° C. The reaction solution became cloudy immediately after mixing.

| | |
|---|---|
| KLH solution | 270 µl (1017 µg) |
| SPAPP solution | 180 µl (1315 µg) |
| EDC solution | 30 µl |

To quench unreacted amino groups, 30 µl of 1 M Tris-HCl (pH 7.0) was added. The solution was diluted two-fold with PBS, dispensed into 10 tubes, and stored at −30° C. until immunization.

(1-2) Immunization

Immunization was performed by mixing the antigen with an equal volume of complete Freund's adjuvant (initial immunization only) or incomplete Freund's adjuvant and by injecting an amount corresponding to about 120 µg of antigen peptide at a time under the skin of two rabbits. Immunization was performed every two weeks from day 0, which is the initial immunization date (four times in total). Blood was sampled on day 49 and an antibody titer of serum was examined by the dot blotting test.

(1-3) Result

An antibody titer to SPAPP was not detected. A possible reason is that since the reaction solution composition was not suitable for maintaining the dissolved state of SPAPP, the production of the conjugate was insufficient.

(2) SPAPP/EWA Conjugate (2-1) Production of Conjugate

Since KLH has lower solubility as a carrier protein, highly soluble egg white avidin (EWA, Wako Pure Chemical Industries, Ltd., No. 017-21011) was selected. EWA was dissolved into pure water at 25 mg/ml to prepare EWA aqueous solution, and SPAPP/EWA DMSO solution was then prepared with the following composition.

(i) EWA DMSO Solution

| | |
|---|---|
| 100% DMSO | 280 μl |
| 1M MES buffer (pH 4.5) | 35 μl |
| EWA aqueous solution | 50 μl |

(ii) SPAPP DMSO Solution

| | |
|---|---|
| 7.5 mg/ml SPAPP/100% DMSO | 135 μl |
| 1M MES buffer (pH 4.5) | 50 μl |
| pure water | 50 μl |

These solutions were mixed in the following volumes and order and allowed to stand for 15 hours at 23° C. The reaction solution became slightly cloudy. To quench unreacted amino groups, 30 μl of 1 M Tris-HCl (pH 7.0) was added. The solution was diluted two-fold with PBS, dispensed into 10 tubes, and stored at −30° C. until immunization.

(iii) SPAPP/EWA Conjugate Solution

| | |
|---|---|
| EWA DMSO solution | 365 μl |
| SPAPP DMSO solution | 250 μl |
| 33 mg/ml EDC | 30 μl |

(2-2) Immunization

Immunization was performed by mixing the antigen with an equal volume of complete Freund's adjuvant (initial immunization only) or incomplete Freund's adjuvant and by injecting an amount corresponding to about 120 μg of antigen peptides at a time under the skin of two rabbits. Immunization was performed every two weeks from day 0, which is the initial immunization date (four times in total). Blood was sampled on day 49 and an antibody titer of serum was examined by the dot blotting.

(2-3) Result

An antibody titer to SPAPP was not detected. A possible reason is that since the reaction solution composition was not suitable for maintaining the dissolved state of SPAPP, the production of the conjugate was insufficient.

(3) SPAPP/HRP Conjugate (3-1) Production of Conjugate

Horseradish peroxidase (HRP, Wako Pure Chemical Industries, Ltd., No. 169-10791) was dissolved into pure water at 50 mg/ml. To remove insoluble impurities, supernatant was collected after 10 minutes of centrifugation at 15,000 rpm. To remove degraded protein, the centrifugal filter unit (Amicon YM-5) having a molecular weight cutoff of 5,000 was used for washing three times.

(i) HRP DMSO Solution

| | |
|---|---|
| 100% DMSO | 280 μl |
| 1M MES buffer (pH 4.5) | 35 μl |
| HRP | 44 μl |
| Pure water | 6 μl |

(ii) SPAPP DMSO Solution

| | |
|---|---|
| 7.5 mg/ml SPAPP/100% DMSO | 135 μl |
| 1M MES buffer (pH 4.5) | 50 μl |
| Pure water | 50 μl |

These solutions were mixed in the following volumes and order and allowed to stand for 15 hours at 23° C. The reaction solution became slightly cloudy. To quench unreacted amino groups, 30 μl of 1 M Tris-HCl (pH 7.0) was added. The solution was diluted two-fold with PBS, dispensed into 10 tubes, and stored at −30° C. until immunization.

(iii) SPAPP/HRP Conjugate Solution

| | |
|---|---|
| HRP DMSO solution | 365 μl |
| SPAPP DMSO solution | 250 μl |
| 33 mg/ml EDC | 30 μl |

(3-2) Immunization

Immunization was performed by mixing the antigen with an equal volume of complete Freund's adjuvant (initial immunization only) or incomplete Freund's adjuvant and by injecting an amount corresponding to about 120 μg of antigen peptides at a time under the skin of two rabbits. Immunization was performed every two weeks from day 0, which is the initial immunization date (four times in total). Blood was sampled on day 49 and an antibody titer of serum was examined by the dot blotting.

(3-3) Result

An antibody titer to SPAPP was not detected. A possible reason is that since the reaction solution composition was not suitable for maintaining the dissolved state of SPAPP, the production of the conjugate was insufficient.

(4) SPAPP/OVA Conjugate

A conjugate reaction is induced between SPAPP and ovalbumin (abbreviated as OVA) in accordance with a procedure described at (ii) to prepare SPAPP/OVA conjugate solution from SPAPP/OVA solution described at (i).

(i) SPAPP/OVA Solution

| | |
|---|---|
| 10M urea, 20 mM Phosphate buffer | 1320 μl |
| 20 mg/ml SPAPP (purity: 94.38%), DMSO solution | 300 μl |
| 20 mg/ml Ovalbumin (Calbiochem, #32467), 10M urea, 20 mM Phosphate buffer | 300 μl |
| 20% Tween 20 | 120 μl |
| DW | 60 μl |
| Total | 2100 μl |

(ii) Procedure

1. After 20 minutes of preincubation of the solution of (i) in a dryer heated to 95° C., 62.5 mM BS3 (Thermo Fisher Scientific)/20 mM Phosphate buffer was added as a cross-linker by 300 μl with vortexing.

2. The solution was then incubated for 2 hours at 95° C.

3. Subsequently, 1 M Tris-HCl (pH 7) was added by 120 μl to quench unreacted BS3 up to 30 minutes at room temperature.

4. The solution of 3. was added dropwise to 7,080 μl of PBS.

Example 1

Acquisition of Antibody Using Antigen of the Present Invention (1), Polyclonal Antibody The titer was measured by dot blotting using serum obtained by a direct immunization method using as immunogen a solution with SPAPP suspended in a solvent containing a nonionic surfactant.

(1) Preparation of Antigen—SPAPP/1% Tween 20

Six (6) mg of SPAPP with the purity of 92% was weighed and suspended in 5.4 ml of pure water. At this point, SPAPP was not dissolved at all in the aqueous solution and became cloudy. The solution was allowed to stand for about 3 hours in this state, and 0.6 ml of 10% Tween 20 was added and mixed. The final concentration of SPAPP was 2 mg/ml. Ultrasound was applied intermittently for about 3 minutes in total by TOMY SEIKO Handy Sonic Model UR-20P at power level 7. The ultrasonic vibrations were applied until the transparency increased to some degree and the absorbance at 600 nm reached about 0.2. The resulting SPAPP solution was dispensed into 10 tubes and stored at −30° C. until immediately before use for immunization.

(2) Immunization

Immunization was performed by mixing the SPAPP solution prepared at (1) with an equal amount of Freund's complete or incomplete adjuvant and by injecting under the skin of twenty Balb/c mice at a dose of 20 µg per individual. Immunization was performed six times in total at intervals of two weeks on schedule and, after one week from the administration of the antigen, intermediate blood sampling or whole blood collection was performed as needed.

(3) Dot Blotting

The SPAPP concentration was adjusted so that each spot of the dot blot described in Test Example 3 contains 10 or 100 ng and the serum of 20 mice obtained at (2) was diluted by a factor of 500 to measure titers.

(4) Result

Figure 3:
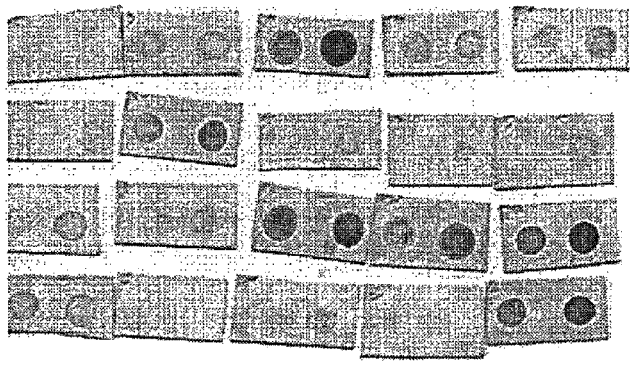
FIG. 3 depicts dot blot of SPAPP using serum (diluted 500-fold) of 20 mice immunized with the method of the present invention.

The result is shown in FIG. 3. Ten (10) ng of SPAPP was detectable with serum of about a half of the 20 mice. Thus, by using the suspension of SPAPP for immunization without conjugation, the serum (polyclonal antibody) having sufficient reactivity to SPAPP was obtained.

Example 2

Particle Size Distribution and Molecular Weight Distribution of SPAPP (1) Measurement of Particle Size Distribution The particle size distribution of the SPAPP/1% Tween 20 suspension used for the immunization mentioned above was examined as follows. After mixing the SPAPP suspension (2 mg/ml) with an equal amount of 0.4% trypan blue solution, the solution was applied to the cell counting device, Countess (registered trademark) (manufactured by INVITROGEN). In this device, 2 µm to 80 µm particles can be measured.

Figure 4:
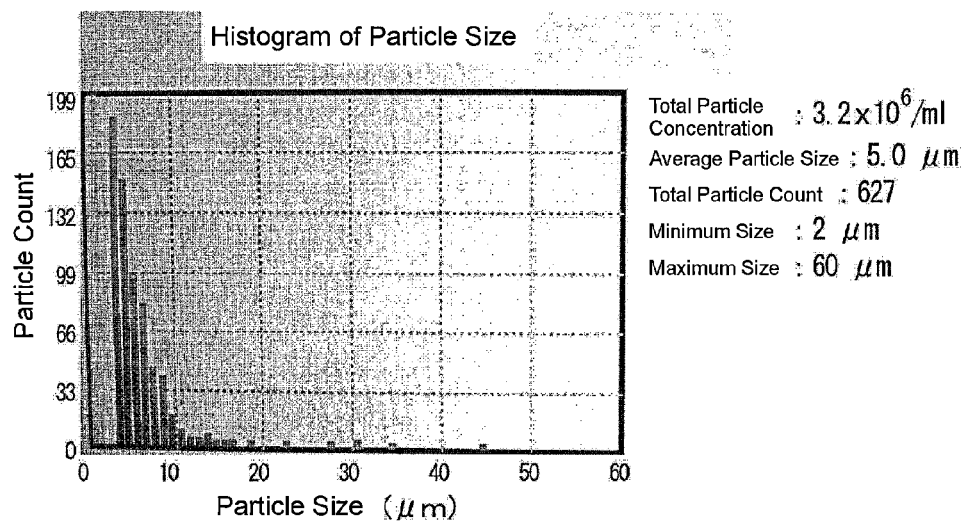
FIG. 4 depicts particle size distribution from Countess (registered trademark) measurement in SPAPP/1% Tween 20 suspension used for immunization.

(2) As a result, the SPAPP particle size distribution in the suspension was from 2 to 60 µm and the concentration was $3.2 \times 10^6$/ml. The majority had a size of a few µm. FIG. 4 shows the measurement result of the molecular weight distribution.

Figure 5:
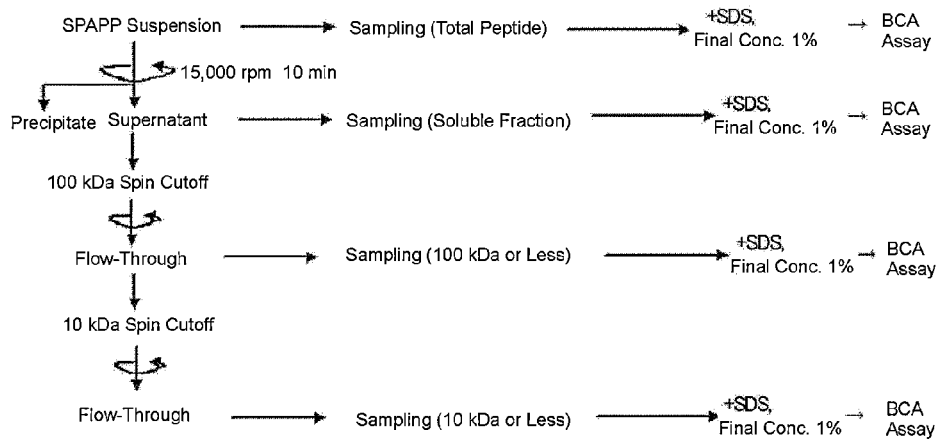
FIG. 5 depicts measurement procedures for the molecular weight distribution of peptide aggregates in SPAPP/1% Tween 20 suspension used for immunization.

The molecular weight distribution of SPAPP aggregates in the suspension was measured in accordance with the following procedure. FIG. 5 shows an outline of this procedure.

(i) The suspension was centrifuged at 15,000 rpm for five minutes and divided into supernatant and precipitate. This centrifugation causes particles equal to or larger than about 1 µm to precipitate.

(ii) The supernatant was applied to a molecular weight 100,000 cutoff spin filter (Amicon Microcon YM-100) and caused to pass through the filter by centrifugation.

(iii) The flow-through solution of (ii) was applied to a molecular weight 10,000 cutoff spin filter and caused to pass through the filter by centrifugation.

On each stage of the process described above, the protein concentration of the solution was measured by the BCA protein assay (Thermo Fisher Scientific) using BSA as the standard.

As a result, since the protein concentration of the supernatant was reduced to about a half of the original solution by the initial centrifugation, it was found that particles equal to or larger than 1 µm (insoluble fraction) accounted for about a half (48% by mass) of the mass of the total protein. It was also found that the remainders were those having a molecular weight of 10,000 to 100,000 (10 to 100 kDa) accounting for 20% by mass and those having a molecular weight equal to or greater than 100,000 (100 kDa) accounting for 33% by mass (Table 2).

TABLE 2

| Molecular Weight Distribution of Peptide Aggregates in SPAPP/1% Tween 20 Suspension | | | | |
|---|---|---|---|---|
| MW | Less than 10 kDa | 10-100 kDa | 100 kDa or more | Insoluble (precipitate) |
| Peptide mass ratio | 0% | 20% | 33% | 48% |

(3) Conclusion

It is found that when SPAPP consisting of 17 amino acids and having the molecular weight of 1781 as a monomer is put into a suspended state in an aqueous solution containing a surfactant as described above, the molecular weight distribution and the particle size distribution are broad.

Example 3

Test for Controlling Molecular Size (Molecular Weight/Particle Size) Distribution of Aggregates (1) Relationship Between Standing Time in Pure Water and Molecular Size Distribution of Aggregates The time from suspension of SPAPP in pure water to addition of various surfactants was changed to confirm that the molecular size distribution of aggregates varies depending on the time. For example, in the case of 1% Tween 20, the insoluble fraction (precipitate) was 5% when the surfactants were added immediately after suspension of SPAPP in pure water, 17% when added after 1.5 hours, and 48% when added after 3 hours.

(2) Molecular Size Distribution in Other Nonionic Surfactant Solutions

Figure 6:
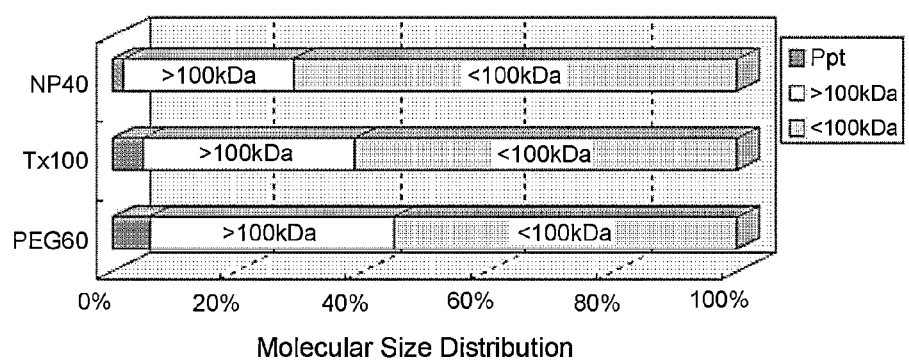
FIG. 6 depicts the molecular weight distribution of SPAPP in nonionic surfactants. A: The surfactants were mixed immediately after suspending SPAPP in pure water. B: The surfactants were added after suspension of SPAPP in pure water was allowed to stand at room temperature for 90 minutes.
Figure 6:
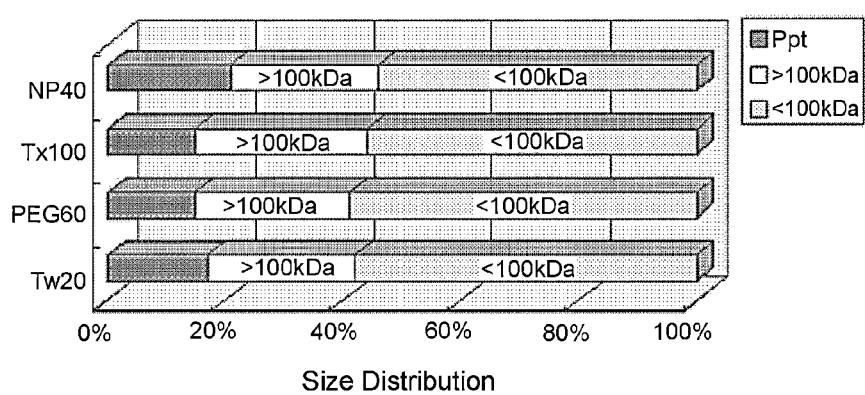

It was examined whether SPAPP forms high-molecular-weight aggregates in other nonionic surfactant solutions. PEG60 dodecyl ether (Polypure), Triton X-100, and Nonidet P-40 were used as surfactants at 1% in each case. As was the case with the method of Example 2, each of the surfactants was used for preparing SPAPP suspension and, after the size fractionation using centrifugation and spin-type molecular weight cutoff filters, 10% SDS was added to and mixed with each of fractions to the final concentration of 1% to dissolve the aggregates. The peptide concentrations of the fractions were measured by the BCA assay and the molecular weight distribution of SPAPP aggregates were summarized as shown in FIGS. 6A and 6B. Histogram A shows the case where the surfactants were mixed immediately after suspension of SPAPP into pure water and histogram B shows the case where the surfactants were added after suspension of SPAPP in pure water was allowed to stand at room temperature for 90 minutes. In the histograms, "Ppt" indicates peptides removed by centrifugation, i.e., precipitate, which is considered to have a size of 1 µm or larger and a molecular weight of several hundred kilodaltons or more. ">100 kDa" indicates 100 kDa or more and "<100 kDa" indicates 100 kDa or less. Although the size distribution is slightly varied depending on the type of surfactant, it was found that high-molecular-weight aggregates are formed with any of the surfactants under the conditions as described above.

(3) Discussion

From (1) and (2) above, it was found that the molecular size (molecular weight/particle size) can be controlled by the type of surfactant and the time of suspension in pure water.

Example 4

Acquisition of Antibody Using Antigen of the Present Invention (2), Monoclonal Antibody Since it was found from Example 1 that an antibody to SPAPP can be obtained with a method without conjugating with a carrier protein, production of monoclonal antibodies was attempted.

(1) Immunization

The antigen was prepared by the method of Example 1 (1) to immunize thirty (30) Balb/c mice. Immunization was performed seven times in total at intervals of two weeks. An equal amount of Titer Max Gold (Titer Max Inc.) was used as adjuvant, and the immunization was performed by injecting the antigen corresponding to 20 µg at a time into the foot pad. Serum on day 77 and day 90 after the start of immunization were tested as follows.

(2) Antibody Titer Measurement by Enzyme Immunoassay (EIA)

(2-1) EIA Test Method (2-1-1) Procedure (i) The SPAPP/OVA conjugate produced by the method of Comparative Example (4) was diluted with PBS to 2.5 µg/ml, added in a volume of 100 µl to wells of Nunc No. 467120 Medisorp, and allowed to stand overnight at 4° C.

(ii) The solution in the wells was aspirated and discarded and 230 µl of 1% BSA/PBST was added and allowed to stand for one hour at room temperature for blocking. After aspirating and removing the blocking solution, 230 µl of 1% BSA/PBS solution was added and allowed to stand for one hour or more at room temperature, and the solution in the wells was then aspirated and discarded.

(iii) Serum diluted by 1% BSA/PBS was added to each of the wells (100 µl/well) and allowed to stand for one hour at room temperature.

(iv) The solution in the wells was aspirated and discarded and the wells were washed six times with 300 µl of PBST (0.1% Tween 20).

(v) POD-labeled anti-mouse IgG (MBL No. 330) diluted by a factor of 4,000 with 1% BSA/PBST was added as secondary antibodies to the wells (100 µl/well) and allowed to stand for one hour at room temperature.

(vi) The solution in the wells was aspirated and discarded and the wells were washed six times with 300 µl of PBST (0.1% Tween 20).

(vii) One hundred (100)µl of TMB (DAKO No. S1599) was added to the wells as a substrate for color development and reacted for 30 minutes at room temperature and an equal amount of 2N sulfuric acid was added to stop the reaction. The absorbance of the reaction solution was measured at 450 nm.

(2-2-2) Result

Figure 7:
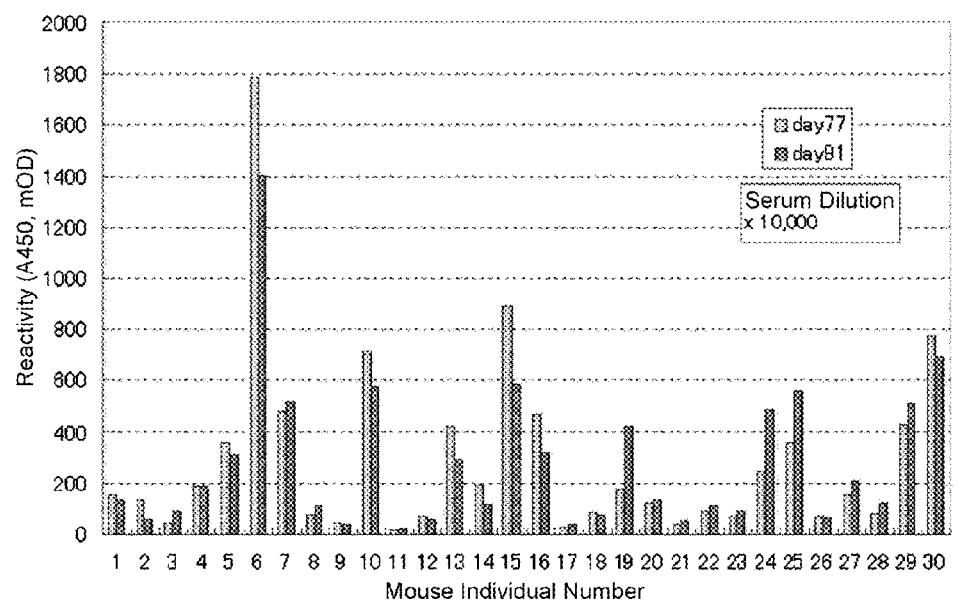
FIG. 7 depicts the result of titer assay with EIA for SPAPP using serum (diluted 10.000-fold) of 30 mice immunized with the method of the present invention.

FIG. 7 depicts titers of the serum diluted by a factor of 10,000 on day 77 and day 90. Although a difference in intensity exists, it was found that the sera of 9 to 10 mice corresponding to about ⅓ of 30 mice had a certain degree of reactivity (400 mOD or more).

(3) Immunofluorescent Staining

For the serum of the individual Nos. 6, 9, and 15 having higher titers in (2) above, immunofluorescent staining was performed by using human neuroblastoma SK-N-SH cells.

(3-1) Procedure

Human neuroblastoma SK-N-SH cells were seeded in MEMα medium in a poly-D-lysine-coated slide chamber (Becton Dickinson No. 354632) and cultured in a 5% $CO_2$ incubator at 37° C.

The following operations were performed on ice:
(i) washing with PBS for five minutes twice;
(ii) immobilization and permeabilization treatment with methanol at −20° C. for five minutes;
(iii) washing with PBS once;
(iv) blocking with 5% goat serum/PBS for one hour;
(v) adding the mouse serum mentioned above diluted by a factor of 250 with 5% goat serum/PBS and allowing to stand for one hour;
(vi) washing with PBS for five minutes three times;
(vii) adding a fluorescent-labeled secondary antibody (Alexa Fluor® 488 Goat Anti-mouse IgG, 2 mg/ml, Invitrogen No. A11001) diluted by a factor of 1,000 with 5% goat serum/PBS and allowing to stand for one hour;
(viii) washing with PBS for five minutes three times;
(ix) adding a color fading inhibitor (ProLong Gold Antifade Reagent with DAPI, Invitrogen, No. P36935) and applying a cover glass; and
(x) taking an image with LSM (ZWEISS META5000).

(3-2) Result of Staining

Figure 8:
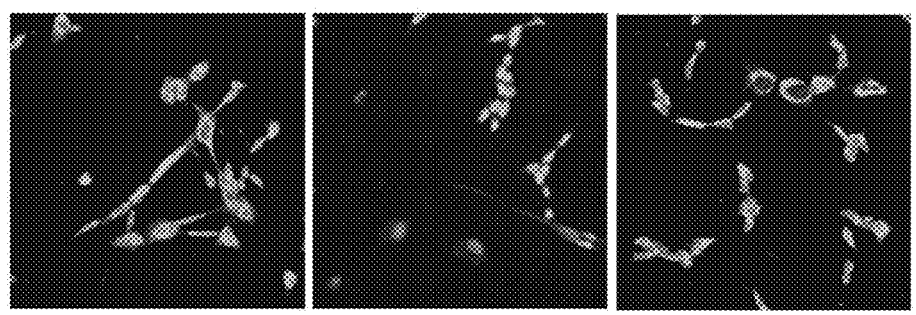
FIG. 8 depicts the immunofluorescent staining of human neuroblastoma SK-N-SH cells using serum of three individuals of FIG. 7. (A) No. 6. (B) No. 10. (C) No. 15.

The result is shown in FIG. 8. In FIG. 8, orange indicates staining based on an antibody response and blue indicates DAPI staining of nuclei.

(4) Production of Monoclonal Antibodies

The spleen lymphocytes of the mice Nos. 6, 10, and 15 were used for cell fusion. The mouse myeloma P3U1 cells were used as a cell line for cell fusion to produce hybridomas with a standard PEG (PEG1500) method described in "*Antibodies; A LABORATORY MANUAL*, Ed Harlow & David Lane, Cold Spring Harbor Laboratory, 1988" and 15 strains of anti-SPAPP antibody-producing hybridoma clones were selected. For selecting the candidate strains, EIA using the SPAPP/OVA-coated plates described in (2) above was performed. Thirteen (13) wells with higher reactivity in EIA were selected. The hybridomas in each of the wells were collected and single clones were selected from each of 96-well plates with a limiting dilution method and grown and cultured in the HAT medium (Invitrogen #11875 RPMI medium 1640, 1% pyruvate, 1% penicillin streptomycin stock, 1×HAT). The cultured cells were washed with PBS and about $1\times10^7$ cells were intraperitoneally administered to pristine-treated Balb/c mice to obtain ascites with a conventional method. HiTrap proteinG column (GE Healthcare)

was used for purifying IgG from the ascites of each mouse with a conventional method. A total of ten types of purified IgG were obtained and named anti-SPAPP monoclonal antibodies CM61, CM101, CM102, CM103, CM152, CM154, CM156, CM157, CM158, and CM159 and used in the following test.

Example 5

Figure 9:
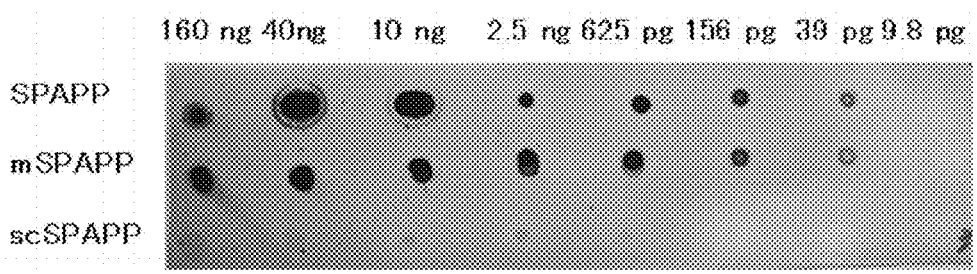
FIG. 9 depicts the result of titer assay with dot blotting for SPAPP using an anti-SPAPP monoclonal antibody CM61 obtained according to the present invention.
Figure 10:
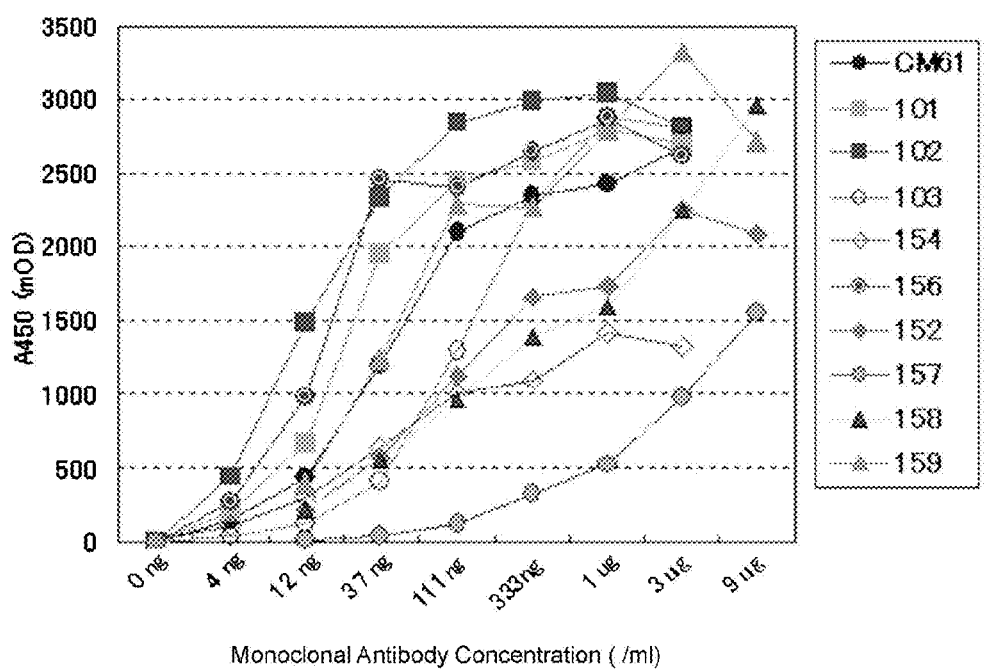
FIG. 10 depicts the result of titer assay with EIA for SPAPP using anti-SPAPP monoclonal antibodies (10 types) obtained according to the present invention.

Analysis of Monoclonal Antibodies of the Present Invention (1) Detection Sensitivity in Dot Blot and Specificity of Recognition Sequence
(1-1) Test Method
The anti-SPAPP monoclonal antibody CM61 obtained in Example 4 (4) was used for dot blot of SPAPP with the method of Test Example 3. Amounts of SPAPP (diluted with 1 Tween 20) infiltrated into spots were amounts shown in FIG. 9 and 10 μg/ml of CM61 was used as a primary antibody. For reference, dot blotting was performed for mouse SPAPP having different amino acids at two positions and for scSPAPP the amino acid composition of which is the same as SPAPP and the sequence of which is scrambled, by using the same amount as that of SPAPP.
(1-2) Result
SPAPP of about 40 pg was detectable. Mouse SPAPP (mSPAPP) was also recognized. This means that the antibody can be used in experiments using mouse cells or individuals. On the other hand, scSPAPP had almost no reactivity even in the case of 160 ng. This means that the obtained antibody has a sequence-specific recognition binding property rather than simply recognizing a hydrophobic amino acid cluster.
(2) EIA
For several anti-SPAPP monoclonal antibodies obtained in Example 4 (4), EIA was performed by using SPAPP/OVA-coated plates.
(2-1) Test Method
Tests were performed in accordance with Example 4 for ten varieties of monoclonal antibodies at SPAPP concentrations of 0 ng, 4 ng, 12 ng, 37 ng, 111 ng, 333 ng, 1 μg, 3 μg, and 9 μg per 1 ml.
(2-2) Result
The result is shown in FIG. 10. In this EIA, it was found that reactivity was detected from about 10 ng/ml in the case of the antibodies with higher reactivity. The results of Examples 1 to 5 demonstrated that polyclonal and monoclonal antibodies with an affinity of practical use and a binding property of sequence-specific recognition were obtained with the immunization method of the present invention using hydrophobic peptide without conjugate.

Example 6

The antibodies of the present invention were used for detecting an antigen (SPAPP) in clinical samples. Human plasma was used as a clinical sample.
(1) Materials and Methods
(i) Preparation of EIA Plate
SPAPP dissolved in 1 Tween 20 at 1 mg/ml was diluted with pure water by a factor of 200, added in a volume of 100 μl to wells of Nunc No. 467120 Medisorp, and allowed to stand overnight at 4° C. The solution in the wells was aspirated and discarded and 230 μl of 1% BSA/PBST was added and allowed to stand for one hour at room temperature for blocking.

Figure 13:
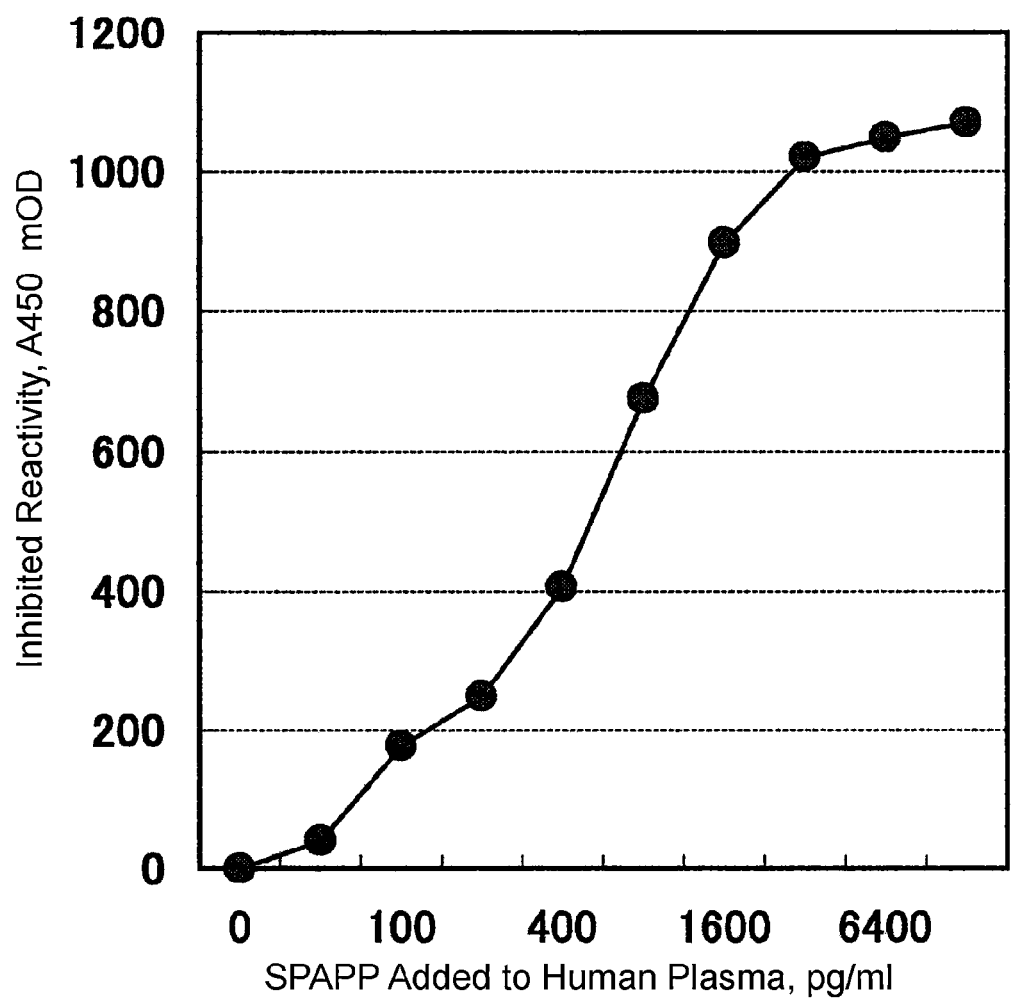
FIG. 13 depicts the result of detection of SPAPP in SPAPP-added human plasma using anti-SPAPP monoclonal antibody CM6 obtained according to the present invention.

(ii) Preparation of SPAPP-Added Human Plasma (Clinical Sample)
After removing large unwanted precipitates with tweezers, human plasma (Kohjin) was centrifuged for 30 minutes at 20,000×g to use the supernatant. One (1) mg/ml SPAPP dissolved in 1% Tween 20 was diluted with 10% BSA/1% Tween 20/PBS to the concentration acquired by multiplying the final concentration indicated in a graph of FIG. 13 by twelve. Ten (10) μl of the diluted SPAPP solution was added to 100 μl of human plasma to obtain SPAPP-added human plasma.
(iii) Preparation of Antibody Solution and Antigen-Antibody Reaction
Among the antibodies used in Example 5, the anti-SPAPP monoclonal antibody CM61 with high EIA activity was diluted with 1 BSA/PBST to 120 ng/ml to prepare anti-SPAPP monoclonal antibody solution. The antibody solution was added to the SPAPP-added human plasma obtained at (ii) (final concentration: 10 ng/ml). An antigen-antibody reaction was performed at room temperature for one hour.
(iv) EIA
One hundred (100) μl of the reaction solution was added to each well of the EIA plate of (i) and allowed to stand for one hour at room temperature.
(v) The solution in the wells was aspirated and discarded and the wells were washed six times with 300 μl of PBST (0.1% Tween 20).
(vi) One hundred (100) μl of POD-labeled anti-mouse IgG (MBL No. 330) diluted by a factor of 4,000 with 1% BSA/PBST was added as secondary antibody to the wells and allowed to stand for one hour at room temperature.
(vii) The solution in the wells was aspirated and discarded and the wells were washed six times with 300 μl of PBST (0.1% Tween 20).
(viii) One hundred (100) μl of TMB (DAKO No. S1599) was added to the wells as a substrate for color development and reacted for 30 minutes at room temperature and an equal amount of 2N sulfuric acid was added to stop the reaction. The absorbance of the reaction solution was measured at 450 nm.
(2) Results and Discussion
The result is shown in FIG. 13. The final concentration of human plasma was 83% in this assay. The final concentration of the anti-SPAPP monoclonal antibody CM61 was 10 ng/ml. In the case of SPAPP-free plasma, the binding of the CM61 antibody to the EIA plate (SPAPP-coated plate) was hardly inhibited by human plasma and, in this assay, the coloration was 1,100 mOD in terms of the absorbance at 450 nm. As the concentration of SPAPP added to the plasma increases, the CM61 antibody first binds to SPAPP in the solution and, therefore, SPAPP in the solution competes with SPAPP on the plate, and the binding of the CM61 antibody to the plate is inhibited. The vertical axis of the graph indicates the degree of inhibition as absorbance. According to this result, it is demonstrated that if at least 200 pg/ml of this antigen is present in human plasma, the antigen is detectable as a difference in absorbance in this EIA system as compared to the case that the antigen is not present. Since the protein concentration in human plasma is 50 to 70 mg/ml, this means that the assay system using the CM61 antibody can detect the presence of the antigen (SPAPP) if it is present in the plasma even at a concentration of one three-hundred millionth (1/300,000,000) of the total protein. It is believed that about 10,000 types of proteins exist in human plasma, including those present in only trace amounts. The result means that even if 10,000 different types of proteins exist together, this assay system can distinguish and detect SPAPP from these proteins.

Example 7

Immunization with Hydrophobic Peptides Other than SPAPP

It was examined whether a hydrophobic peptide consisting of another sequence would enable the acquisition of an antibody having reactivity to the hydrophobic peptide acting as an antigen from immunization without a conjugate as was the case with SPAPP. The test method followed that of Example 1.

(1) Synthesis of Hydrophobic Peptides

The following (i) and (ii) were selected as hydrophobic peptides to produce synthetic peptides with the purity of 70 to 80%:

(i) *Escherichia coli* outer membrane protein ompA-derived sequence, FGGYQVNPYVGFEMGYDWLGRMPY (FCG24/SEQ ID NO: 2); and (ii) human CD133-derived sequence, FLFCWILMILVV-LTFVVGANVEK (FLF23/SEQ ID NO: 3).

(2) Preparation of Antigen

The hydrophobic peptides of (1) were added to 1% Tween 20 to prepare suspensions. The presence of large particles of the hydrophobic peptides in the respective suspensions was confirmed by a dynamic light scattering particle size analyser (NIKKISO Nanotrac UPA-UT151) or Countess.

Figure 11:
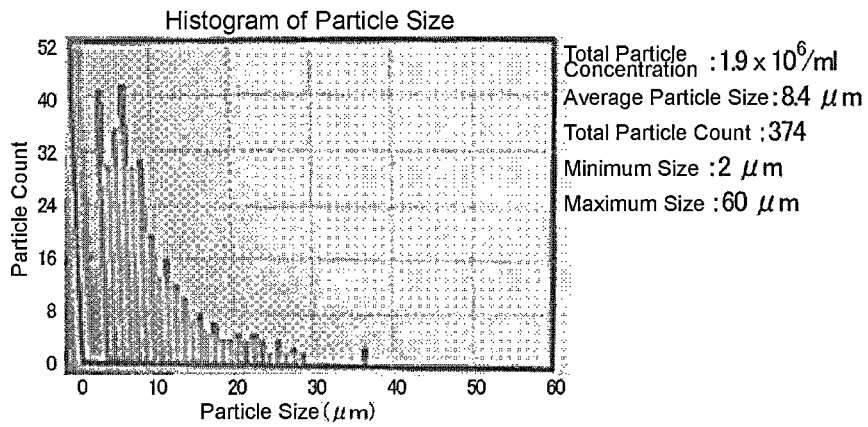
FIG. 11 depicts the particle size distribution of 1 Tween 20 suspensions of peptides FCG24 and FLF23. (A) A result from Countess (registered trademark) measurement of the peptide FCG24 in 1 Tween 20 suspension. (B) A measurement result of 1% Tween 20 suspension from a dynamic light scattering particle size analyser. (C) A measurement result of peptide FLF23 in 1 Tween 20 suspension from a dynamic light scattering particle size analyser.
Figure 11:
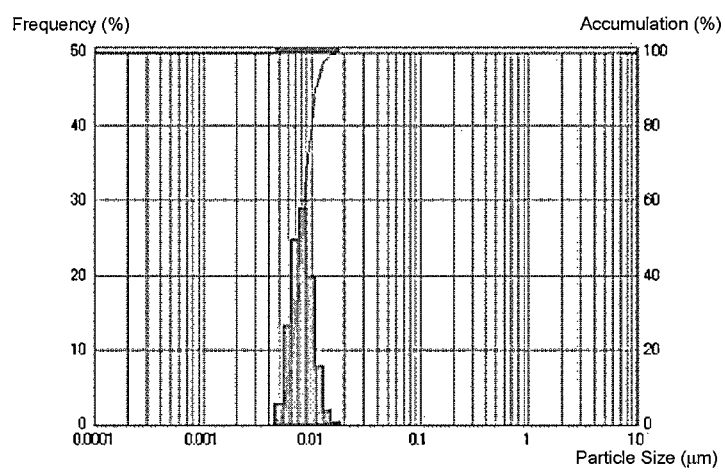
Figure 11:
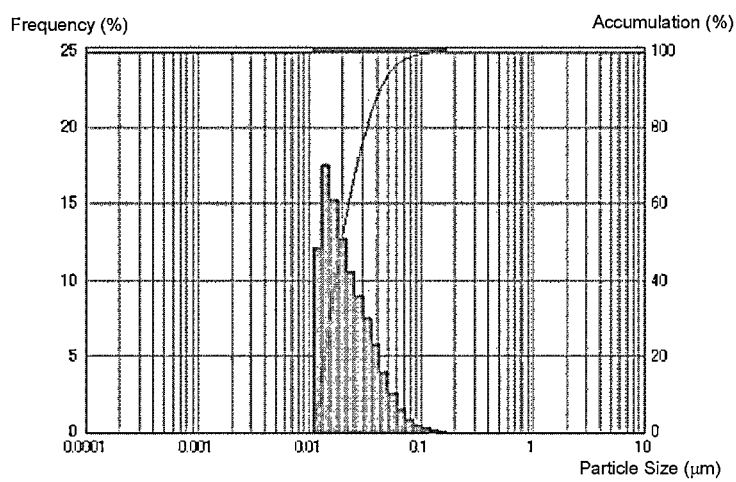

Although the particles cannot be confirmed in the FCG24 suspension by the dynamic light scattering particle size analyser because signals overlap with signals of only the 1 Tween 20 solution (FIG. 11B), cell-sized particles (5 to 35 μm) was confirmed by Countess (registered trademark) (FIG. 11A).

In the FLF23 suspension, particles with sizes larger than the signals of only the 1% Tween 20 solution were confirmed (FIG. 11C).

(3) Immunization

Two (2) mg/ml of each of the suspensions obtained at (2) above was used for immunizing 10 mice and serum was collected after 60 days (#1 to #10).

(4) EIA

EIA was performed by using plates coated with the peptide (i) or (ii) above (5 μg/ml each).

(5) Result

Figure 12:
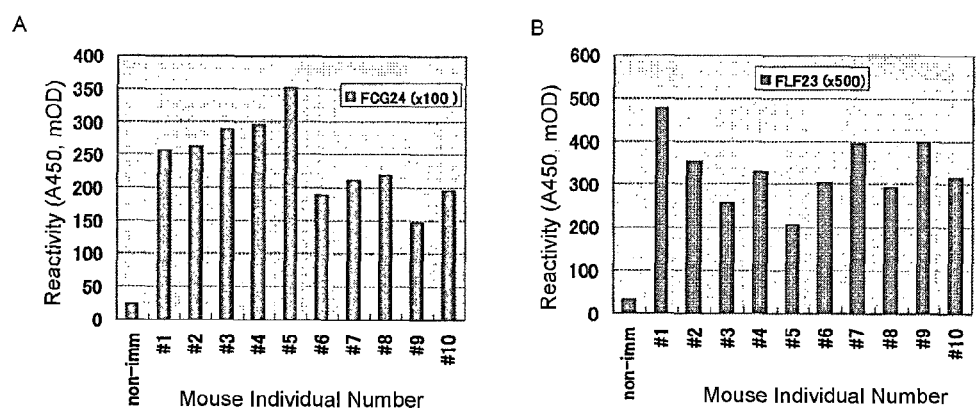
FIG. 12 depicts the result of titer assay with EIA for antigen peptides using serum of mice immunized by 1 Tween 20 suspensions of the peptides FCG24 (A) and FLF23 (B).

The results are shown in FIG. 12.

FCG24 and FLF23 had high reactivity in 100-fold diluted serum and 500-fold diluted serum, respectively, as compared to non-immune mouse serum ("non-imm" in FIG. 12).

From these results, it was found that by using the method of preparing an antigen of the present invention, an anti-hydrophobic peptide antibody can be obtained for other hydrophobic peptides without using a conjugate.

INDUSTRIAL APPLICABILITY

Since the present invention enables the acquisition of an antibody to a hydrophobic peptide, new useful information on hydrophobic signal peptides and membrane proteins, in terms of physiological roles such as metabolic pathways, subcellular localization and interaction partners, which has previously not been available can be obtained. The useful information obtained in this way is highly likely to contribute to the understanding of cellular functions and the development of diagnostic reagents and pharmaceutical agents. Although the acquisition of an antibody to a membrane protein is not easy in a conventional manner, the present invention will effectively and significantly reduce the effort and cost.

The invention claimed is:

1. A method of preparing an antigen without using a carrier protein, the method comprising:
   suspending a hydrophobic peptide in pure water to obtain a pure water suspension of the hydrophobic peptide;
   allowing the obtained suspension to stand for at least 3 hours;
   optionally applying ultrasound to the obtained suspension;
   adding a nonionic surfactant to the suspension at a final concentration of 1 to 2% by mass;
   optionally applying ultrasound to the suspension having a nonionic surfactant;
   producing high molecular-weight aggregates of the hydrophobic peptide;
   mixing the high molecular-weight aggregates of the hydrophobic peptide with adjuvant; and
   obtaining the antigen,
   wherein
   the sequence of the hydrophobic peptide is MLPGLALLLLAAWTARA (SEQ ID NO: 1), FGGYQVNPYVGFEMGYDWLGRMPY (SEQ ID NO: 2), or FLFCWILMILVVLTFVVGANVEK (SEQ ID NO: 3),
   the nonionic surfactant is at least one selected from the group consisting of polyoxyethylene (20) sorbitan monolaurate, polyoxyethylene (20) sorbitan monooleate, polyoxyethylene (8) octylphenyl ether, polyoxyethylene (9) octylphenyl ether, polyethylene glycol (12), polyethylene glycol (24), polyethylene glycol (60) dodecyl ether, and polyethylene glycol cholesterol, and
   each of the aggregates is formed from several or more peptides non-covalently bound to each other and has a molecular weight equal to or greater than 10,000.

2. The method of preparing an antigen according to claim 1, wherein the nonionic surfactant is at least one selected from the group consisting of polyoxyethylene (20) sorbitan monolaurate and polyoxyethylene (20) sorbitan monooleate.

3. The method of preparing an antigen of claim 1, wherein high-molecular-weight aggregates of hydrophobic peptide having a molecular weight equal to or greater than 100,000 account for 20% by mass or more of a total peptide amount in the molecular weight distribution of the suspension containing the nonionic surfactant.

* * * * *